United States Patent [19]

Braude

[11] Patent Number: 5,549,201
[45] Date of Patent: Aug. 27, 1996

[54] PACKAGE FOR DENTAL FLOSS

[76] Inventor: Laurence S. Braude, 797 Kimballwood La., Highland Park, Ill. 60035

[21] Appl. No.: 484,141

[22] Filed: Jun. 7, 1995

[51] Int. Cl.$^6$ ................................................. A61C 15/04
[52] U.S. Cl. ...................... 206/388; 206/63.5; 206/823
[58] Field of Search .................................. 132/323, 324, 132/309; 206/63.5, 388, 581, 823

[56] References Cited

U.S. PATENT DOCUMENTS

| | | |
|---|---|---|
| 2,083,398 | 6/1937 | Roland . |
| 4,530,129 | 7/1985 | Labick et al. ...................... 206/63.5 X |
| 4,579,221 | 4/1986 | Corella . |
| 4,693,365 | 9/1987 | Corella . |
| 4,712,572 | 12/1987 | Hovel, III . |
| 4,852,728 | 8/1989 | Court . |
| 4,934,523 | 6/1990 | Strom . |
| 4,972,946 | 11/1990 | Whittaker . |
| 4,986,289 | 1/1991 | McWhorter . |
| 5,024,324 | 6/1991 | Whittaker . |
| 5,119,941 | 6/1992 | Lepie . |
| 5,129,514 | 7/1992 | Lilley, Jr. ............................... 206/388 |
| 5,322,077 | 6/1994 | Corella . |

FOREIGN PATENT DOCUMENTS 660996  3/1965  Belgium .

Primary Examiner—Jacob K. Ackun
Attorney, Agent, or Firm—Fitch, Even, Tabin & Flannery

[57] ABSTRACT

A plurality of packages of dental floss are provided including a plurality of separate elongate enclosures. The enclosures each have a width and a length with the length being at least nine times as great as the width. The separate enclosures are each independently movable from the other enclosures. A piece of dental floss is individually sealed in each enclosure.

13 Claims, 1 Drawing Sheet

U.S. Patent
Aug. 27, 1996
5,549,201
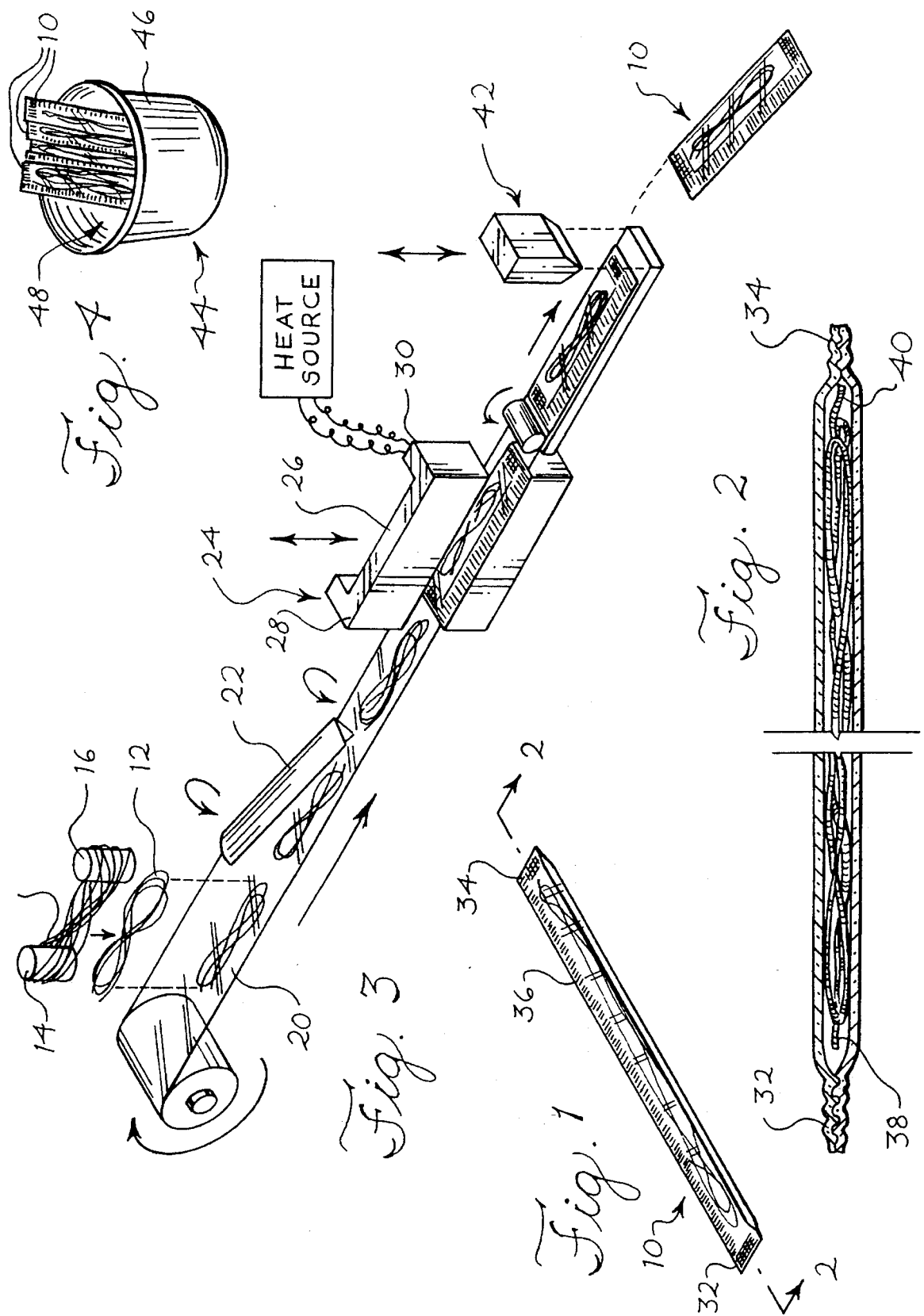

PACKAGE FOR DENTAL FLOSS

FIELD OF THE INVENTION

The present invention relates to packages for dental floss and, more particularly, to a plurality of separate elongate dental floss packages.

BACKGROUND OF THE INVENTION

It is known for food establishments to provide individually packaged toothpicks for use after meals. The toothpicks are generally contained in an elongate paper or plastic enclosure substantially conforming to the length of the toothpick. In this manner, toothpicks can be gratuitously provided in a generally sanitary and inexpensive fashion to patrons after each meal.

Commonly, dental floss is provided to the end user in a relatively rigid plastic housing containing a spool upon which a length of dental floss sufficient for multiple uses is wrapped. A small cutting blade is normally provided on the housing adjacent one side of the spool such that a free end can be dispensed from the spool past the blade until a sufficient length of dental floss has been taken off the spool before the piece of floss is cut at the blade for use. Typically, such a plastic container is kept at home in the medicine cabinet for use at home. While such a plastic container is suitable for home use, it is not economical for food establishments to gratuitously provide such a container to their patrons for use after meals.

SUMMARY OF THE INVENTION

In accordance with the present invention, a plurality of packages of dental floss are provided which are suitable for use by food establishments and the like.

In one form of the invention, the packages include multiple, separate elongate enclosures having a width and a length. The length is at least nine times as great as the width. The separate enclosures are each independently moveable from the other enclosures. A piece of dental floss is individually sealed in each enclosure.

The enclosure length is preferably approximately three and one-half inches (3½") and the enclosure width is preferably approximately three-eighths of an inch (⅜").

The dental floss pieces can each be configured in the shape of a figure-eight ("8") in the enclosures.

The enclosures can be formed from a flexible plastic material.

In one form, the pieces of dental floss each have ends that are freely moveable in the enclosures.

The pieces of dental floss each are of a predetermined length. The length is preferably sized sufficiently for a single use.

In another form, the packages are provided in combination with a cup-shaped container having a wall defining a dental floss package receiving space and an opening through which the packages can be removed from the space. The wall preferably has a height that is less than the length of the plastic enclosures so that the enclosures can project through the container opening as they rest in the container.

BRIEF DESCRIPTION OF THE DRAWINGS

FIG. 1 is a perspective view of a package of dental floss according to the present invention;

FIG. 2 is a cross-sectional view taken along line 2—2 of FIG. 1;

FIG. 3 is a schematic view of a production line for heat-sealing the packages with a piece of dental floss therein; and FIG. 4 is a perspective view of a plurality of dental floss packages in a cup dispenser.

DESCRIPTION OF THE PREFERRED EMBODIMENTS

FIG. 1 illustrates an elongate package 10 containing a piece of dental floss 12 therein. The package 10 is of the type normally used to contain individual toothpicks, and as such, has a length that is several times greater than its width. Preferably, the length of the package 10 is at least nine (9) times greater than the width and can be approximately three and one-half inches (3½") while the width is approximately three-eighths of an inch (⅜"). The dental floss package 10 can be formed by a variety of means, as will be apparent to one skilled in the art. FIG. 3 schematically illustrates one method of forming the packages 10 according to the present invention. The dental floss piece 12 can be wound on two spools 14 and 16 and removed therefrom to be placed in the package 10 such that the dental floss piece 12 substantially has a figure-eight ("8") shape in the package 10. In this manner, greater lengths of dental floss pieces can be provided in the packages 10 than if the pieces were simply unconfigured. On the other hand, the dental floss piece 12 need only be sized such that it is sufficient for single-use, i.e., to be disposed of after it is used, as is needed by patrons of food establishments. In this manner, restaurant owners do not gratuitously provide unnecessarily long pieces of dental floss to restaurant patrons as otherwise patrons would be throwing away pieces of floss having significant lengths of unused portions thereon. The length of dental floss should be at least three inches long, and is preferably between 12 inches and 36 inches, with 24 inches being considered an optimal length.

The package 10 can be formed from a flexible material, such as paper or plastic, as is used with individually-wrapped toothpicks. When paper is used, the seams of the package 10 can be sealed by the use of small amounts of adhesive, as is known.

In the preferred and illustrated form, a transparent plastic material is utilized. To form the packages 10, a roll 18 of plastic material is provided. The plastic sheet 20 dispensed from the roll 18 should have a width that is at least twice as great as the final width of the package 10. As the plastic material is dispensed from the roll 18, the figure-eight ("8") piece of dental floss 12 can be dropped from the spools 14 and 16 onto the sheet 20 which then travels past a folding mechanism such as sheet folding guide 22 causing sheet 20 to be folded over the figure-eight ("8") dental floss piece 12 and onto itself.

Thereafter, the folded over sheet including the dental floss piece 12, passes a heat sealing mechanism 24. The illustrated heat sealer 24 includes identical upper and lower parts, each having a lengthwise portion 26 and leg portions 28 and 30 at either end thereof. Thus, with a piece of floss 12 positioned between the end portions 28 and 30, the heat sealer upper and lower parts are timed to close against each other and apply heat to seal the elongate package 10 at spaced ends 32 and 34 thereof and along the open length 36 thereof opposite from the fold. The length of the figure-eight ("8") piece 12 and the timing and configuration of the heat sealer 24 is such that preferably ends 38 and 40 of the figure-eight ("8") dental floss piece 12 remain freely movable in the package 10 after being heat sealed. In this manner, the packages 10 need not be broken at the end seams to remove the dental floss therefrom and, instead, the packages 10 can be broken at any point and still allow for easy removal of the dental floss piece 12. After sealing the dental floss piece 12 in the package 10, the packages 10 pass a cutter 42 to separate the packages 10 one from another.

After forming the package 10, several of the packages can be placed in a cup-shaped dispenser 44 as is commonly done in restaurants with individually-packaged toothpicks. The cup 44 is preferably small enough so that the packages 10 extend outwardly therefrom. More specifically, the annular wall 46 of the cup 44 preferably has a height which is shorter than the length of the packages 10 so that the packages 10 extend through the opening 48 of the cup 44 as they rest in the cup 44 thereby being easily accessed and removed from the cup 44 by food establishment patrons.

The foregoing disclosure and specific embodiments described herein are intended to be illustrative of the broad concepts comprehended by the invention.

What is claimed is:

1. In combination, a plurality of packages of dental floss and a cup-shaped container holding said packages, the packages comprising:

a plurality of separate elongate enclosures having a width and a length with the length being at least nine times as great as the width and the separate enclosures each being independently movable from the other enclosures and separate from one another; and a piece of dental floss sized for a single use, having a length of at least 3 in. and less than 36 in., individually sealed in each enclosure;

each enclosure containing only said single piece of dental floss;

said cup-shaped container having a wall defining a dental floss package receiving space and opening through which the packages can be removed from the space, said wall having a height that is less than the length of the plastic enclosures so that the enclosures can project through the container opening as they rest in the container.

2. The packages of claim 1 wherein the enclosure length is approximately three and one-half inches and the enclosure width is approximately three-eighths of an inch.

3. The packages of claim 1 wherein the dental floss pieces are each configured in the shape of a figure-eight in the enclosures.

4. The packages of claim 1 wherein the enclosures are formed from a flexible plastic material.

5. The packages of claim 1 wherein the pieces of dental floss each have ends thereof with the ends being freely movable in the enclosures.

6. The packages of claim 1 wherein the pieces of dental floss each are of a predetermined length with the length being sized sufficiently for a single use.

7. In combination, a plurality of packages of dental floss and a dispenser for holding said packages in a food establishment;

each package comprising an elongate enclosure having a predetermined width and having a predetermined length at least nine times as great as the width;

a single piece of dental floss sized for a single use having a length of at least 3 in. and less than 36 in. being disposed within each said package;

each said package containing only said single piece of dental floss;

each said package being independently movable and separate from other packages;

said packages being at least partially disposed within said dispenser;

said dispenser being configured for use in a food establishment to enable the packages of dental floss to be easily accessed and removed therefrom.

8. The combination in accordance with claim 7 wherein each said single piece of dental floss has a length of between 12 in. and 36 in.

9. The combination in accordance with claim 8 wherein each said single piece of dental floss has a length of about 24 in.

10. The combination in accordance with claim 9 wherein each said package has a fold along one side and a seal along the length thereof opposite the fold.

11. A combination in accordance with claim 7 wherein each said single piece of dental floss has a figure eight shape.

12. A combination in accordance with claim 7 wherein said dispenser has an annular wall defining an opening and having a height which is shorter than the length of the packages so that the packages extend through the opening as they rest in the dispenser.

13. A combination in accordance with claim 12 wherein each said package is made of a transparent plastic material.

* * * * *